United States Patent
Von Angerer et al.

[11] Patent Number: 6,147,105
[45] Date of Patent: Nov. 14, 2000

[54] 2-PHENYLINDOLES AS ANTIESTROGENIC PHARMACEUTICAL AGENTS

[75] Inventors: Erwin Von Angerer, Pentling; Christian Biberger, Saal; Martin Schneider, Berlin, all of Germany

[73] Assignee: Schering Aktiengesellschaft, Germany

[21] Appl. No.: 08/776,151

[22] PCT Filed: Jul. 27, 1995

[86] PCT No.: PCT/EP95/03000

§ 371 Date: May 14, 1997

§ 102(e) Date: May 14, 1997

[87] PCT Pub. No.: WO96/03375

PCT Pub. Date: Feb. 8, 1996

[30] Foreign Application Priority Data

Jul. 27, 1994 [DE] Germany ............... 44 26 625

[51] Int. Cl.[7] ............... A61K 31/403; C07D 209/82
[52] U.S. Cl. ............... 514/410; 514/397; 514/339; 514/418; 548/420; 548/311.4; 548/484; 546/276.7
[58] Field of Search ............... 548/420, 311.4; 514/410, 397, 339; 546/276.7

[56] References Cited

PUBLICATIONS

Annals of the New York Academy of Sciences vol. 761 p. 178–180, 1995.

CA 107:39609, Kenlo et al., 1987.

CA 76: 14338, Kametani, 1972.

*Primary Examiner*—Jane Fan
*Attorney, Agent, or Firm*—Millen, White, Zelano & Branigan, P.C.

[57] ABSTRACT

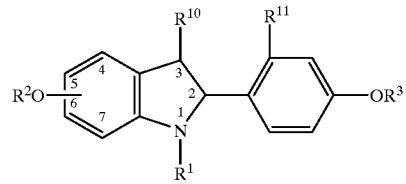

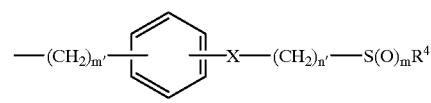

Novel 2-phenyl indoles are disclosed of general formula (I), wherein: $R^1$ represents one of the rests $-(CH_2)_n-S(O)_m-R^4$, $-(CH_2)_n-NR^6-SO_2-R^4$, (a), and n' being integers between 4 and 12 and m and m' are 0, 1 or 2; X represents a methylene group, an imino group $=NR^6$, or an oxygen or sulphur atom; $R^2$ and $R^3$ independently of one another represent a hydrogen atom, a $C_1-C_{10}$ alkyl group, a benzyl, alkanoyl or alkanoyloxy, or carbamoyl rest of formula $-C(O)R^5$ or $-C(O)NR^6R^7$ or a tetrahydropyranyl group; $R^4$ represents a hydrogen atom, a $C_1-C_{10}$ alkyl, a completely or partially fluorinated alkyl group $-(CH_2)_o-(CF_2)_pCF_3$, o and p being independently of one another integers between 0 and 6, an (alkyl)amino or (alkyl)carbamoyl group of formula $(CH_2)_q-Y-NR^8R^9$, q being an integer between 0 and 6 and Y representing a direct bond, a methylene or carbamoyl group (a condition being that q cannot be 0 when Y is a carbonyl group and m is 2), an aryl, aralkyl or heteroaryl group; $R^5$ represents a $C_1-C_{10}$ alkyl group or a $C_1-C_{10}$ alkoxy group, a phenyl or benzyl group; $R^6$, $R^7$, $R^8$ and $R^9$ independently of one another represent a hydrogen atom, a $C_1-C_{10}$ alkyl group, or a benzyl group; and $R^{10}$ represents a methyl group and $R^{11}$ represents a hydrogen atom, or $R^{10}$ and $R^{11}$ both represent a di-, tri- or tetramethylene bridge which can also have a C—C double bond at any location in the bridge. These novel compounds have strong and selective anti-oestrogen properties and are suitable for use in particular in the treatment of oestrogen-related diseases.

22 Claims, No Drawings

2-PHENYLINDOLES AS ANTIESTROGENIC PHARMACEUTICAL AGENTS

This invention relates to 2-phenylindoles, a process for their production, pharmaceutical preparations that contain the latter as well as their use for the production of pharmaceutical agents.

The new 2-phenylindoles are reproduced by general formula I

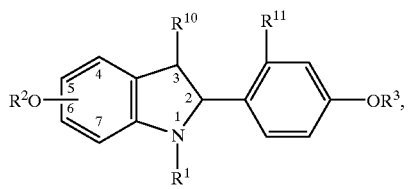

in which

R$^1$ means one of the radicals —(CH$_2$)$_n$—S(O)$_m$—R$^4$, —(CH$_2$)$_n$—NR$^6$—SO$_2$—R$^4$, —(CH$_2$)$_m$,

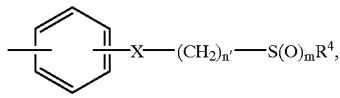

whereby n and n' are integers from 4 to 12 and m and m' are 0, 1 or 2, and X stands for a methylene group, an imino group =NR$^6$, an oxygen or sulfur atom, R$^2$ and R$^3$, independently of one another, mean a hydrogen atom, a C$_1$ to C$_{10}$ alkyl group, a benzyl, alkanoyl or alkanoyloxy or carbamoyl radical of formula —C(O)R$^5$ or —C(O)NR$^6$R$^7$ or a tetrahydropyranyl group, R$^4$ means a hydrogen atom, a C$_1$ to C$_{10}$ alkyl group, a completely or partially fluorinated alkyl group —(CH$_2$)$_o$—(CF$_2$)$_p$CF$_3$, whereby o and p, independently of one another, are in each case an integer from 0 to 6, an (alkyl)amino or (alkyl)carbamoyl group of formula —(CH$_2$)$_q$—Y—NR$^8$R$^9$, whereby q is an integer from 0 to 6 and Y stands for a direct bond, a methylene or carbonyl group, but if Y means a carbonyl group and m is 2, q cannot be 0, an aryl, aralkyl or heteroaryl radical, R$^5$ means a C$_1$ to C$_{10}$ alkyl or C$_1$ to C$_{10}$ alkyloxy group, a phenyl or benzyl radical, R$^6$, R$^7$, R$^8$ and R$^9$, independently of one another, mean a hydrogen atom, a C$_1$ to C$_{10}$ alkyl or benzyl group, and R$^{10}$ means a methyl group and R$^{11}$ means a hydrogen atom or R$^{10}$ and R$^{11}$ together mean a di-, tri- or tetramethylene bridge, which also can have a C—C double bond anywhere in the bridge.

As alkyl groups with 1 to 10 carbon atoms for radicals R$^2$, R$^3$, R$^4$, R$^5$, R$^6$, R$^7$, R$^8$ and R$^9$, the radicals methyl, ethyl, propyl, butyl, pentyl, hexyl, hepty, octyl, nonyl and decanyl and also their branched-chain variants, for example the isopropyl, isobutyl or tert-butyl radicals, are suitable. Cycloalkyl groups with 3 to 10 carbon atoms, and among them especially the cyclopentyl or cyclohexyl radical, can also be mentioned.

A phenyl, 1- or 2-naphthyl radical can stand for an aryl radical R$^4$; primarily a benzyl radical, but also a phenethyl, 1- or 2-naphthylmethyl radical can stand for an aralkyl radical R$^4$; and mainly a 2-, 3- or 4-pyridinyl radical or an imidazolyl radical, which can carry a low alkyl group (C$_1$–C$_4$), for example a methyl group, but also a 2-pyrazine, 2-, 4- or 5-pyrimidine, 3-pyrazine as well as a 2- or 3-thiophene radical on the nitrogen atom can stand for a heteraryl radical R$^4$.

If R$^5$ is to be a C$_1$–C$_{10}$ alkoxy radical, this is primarily a methoxy, ethoxy, n- or isopropoxy, n-, iso- or tert-butoxy radical.

n or n' preferably stands for an integer from 6 to 12, m can be 0, 1 or 2, all indicated meanings are equally possible for o and p; the combinations o=3 and p=1 as well as o=0 and p=0 are to be emphasized for the partially fluorinated alkyl radical R$^4$; finally, q is preferably selected from the range of 2 to 5.

Radicals R$^2$ and R$^3$ preferably each represent a hydrogen atom.

The meanings of n, n', m, m', R$^4$ with o, p, q, Y, R$^8$ and R$^9$ and R$^6$ are selected together such that R$^1$ preferably forms one of the following side chains:

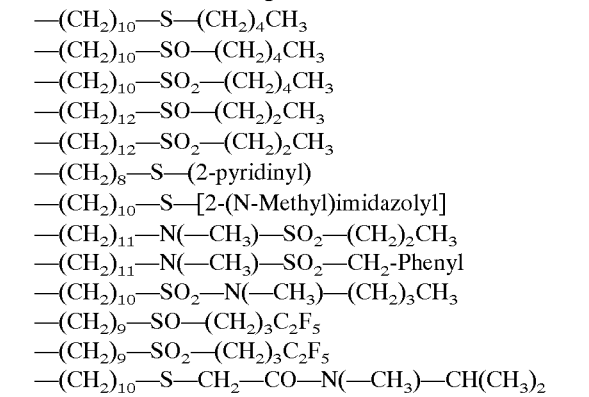

Radical —OR$^2$ can be present in the 4-, 5-, 6- or 7-position of the bicyclic compound of the phenylindole (benzo[a]carbazole).

Especially preferred are those compounds of general formula I in which radical —OR$^2$ is bound to carbon atom 5.

The compounds that are mentioned below are preferred within the scope of this invention:

6,11-dihydro-3,8-dihydroxy-5H-1-[10-(pentylthio)-decyl]benzo[a]carbazole 6,11-dihydro-3,8-dimethoxy-5H-1-[10-(pentylsulfonyl)-decyl]benzo[a]carbazole 5-methoxy-2-(4-methoxyphenyl)-3-methyl-1-[10-(pentylthio)-decyl]-indole 5-methoxy-2-(4-methoxyphenyl)-3-methyl-1-[10-(pentylsulfonyl)-decyl]-indole 5-methoxy-2-(4-methoxyphenyl)-3-methyl-1-[12-(propylsulfonyl)-dodecyl]-indole 5-methoxy-2-(4-methoxyphenyl)-3-methyl-1-[9-(4,4,5,5,5-pentafluoropentylsulfinyl)-nonyl]-indole 1-[10-(n-butyl-methylsulfamoyl)-decyl]-5-methoxy-2-(4-methoxyphenyl)-3-methylindole 5-methoxy-2-(4-methoxyphenyl)-3-methyl-1-[8-(2-pyridinylthio)-octyl]-indole 5-methoxy-2-(4-methoxyphenyl)-3-methyl-1-[11-(N-methyl-propylsulfonamido)-undecyl]-indole 5-methoxy-2-(4-methoxyphenyl)-3-methyl-1-[11-(N-methyl-phenylmethanesulfonamido)-undecyl]-indole 1-(6-mercaptohexyl)-5-methoxy-2-(4-methoxyphenyl)-3-methylindole 1-{6-[3'-(n-butyl-methylcarbamoyl)-propylthio]-hexyl}-5-methoxy-2-(4-methoxy-phenyl)-3-methylindole 5-hydroxy-2-(4-hydroxyphenyl)-3-methyl-1-[12-(propylsulfinyl)-dodecyl]-indole 6,11-dihydro-3,8-dimethoxy-5H-1-[10-(pentylthio)-decyl]benzo[a]carbazole 6,11-dihydro-3,8-dimethoxy-5H-1-[10-(pentylsulfonyl)-decyl]benzo[a]carbazole 5-hydroxy-2-(4-hydroxyphenyl)-3-methyl-1-[12-[2-(N-methyl-imidazolyl)thio]-decyl]-indole 5-hydroxy-2-(4-hydroxyphenyl)-3-methyl-1-[10-[(methyl-iso-propylcarbamoyl)-methylthio]-decyl]-indole 6,11-dihydro-3,8-dihydroxy-5H-1-[10-(pentylsulfinyl)-decyl]benzo[a]carbazole 6,11-dihydro-3,8-dihydroxy-5H-1-[9-(4,4,5,5,5-pentafluoropentylsulfinyl)-nonyl]benzo[a]carbazole 6,11-dihydro-3,8-dihydroxy-5H-1-[9-(4,4,5,5,5-pentafluoropentylsulfonyl)-nonyl]benzo[a]carbazole 6,11-dihydro-3,8-dihydroxy-5H-1-[10-(pentylmethylsulfamoyl)-decyl]benzo[a]carbazole 6,11-dihydro-3,8-dihydroxy-5H-1-[10-[2-(N-methyl-imidazolyl)thio]-decyl]benzo[a]carbazole 5-hydroxy-2-(4-hydroxyphenyl)-3-methyl-1-[4-[4-(pentylsulfonyl)butoxy]-phenyl]-indole 5-hydroxy-2-(4-hydroxyphenyl)-3-methyl-1-[4-[4-(pentylsulfonyl)butoxy]-benzyl]-indole 5-hydroxy-2-(4-hydroxyphenyl)-3-methyl-1-[4-[4-(pentylsulfonyl)butyl]methylamino]-phenyl]-indole Especially to be emphasized within the scope of this invention are those compounds of general formula I, in which $R^{10}$ together with $R^{11}$ stand for an ethano or etheno bridge. For these compounds, the radicals $R^1$ that are already mentioned above also are regarded as preferred.

It has been found that the compounds of general formula I according to the invention have strong antiestrogenic properties (competitive antiestrogens). Compounds with antiestrogenic properties, i.e., substances with inhibiting actions compared to estrogens, were already described in the literature.

As antiestrogens, for example, tamoxifen can be cited (Eur. J. Cancer Clin. Oncol. 1985, 21, 985 and J. S. Patterson, "10 Years of Tamoxifen in Breast Cancer" in Hormonal Manipulation of Cancer; Peptides, Growth Factors and New (Anti)steroidal Agents, Raven Press, New York (1987)).

Steroidal antiestrogens are described in European Patent Application 0 138 504. Antiestrogenic indole derivatives are already known from German Patent 32 32 968, from J. Med. Chem. 1983, 26, 113; J. Med. Chem., 1984, 27, 1439, Eur. J. Cancer. Clin. Oncol. 1985, 21, 531 and Cancer Treatment Reviews 1984, 11, 147 as well as N-aminoalkylindoles, which in addition to pronounced antiestrogenic action exhibit only slight estrogenic activity, from European Patent Application 0 348 341.

Hydroxylated 2-phenylindoles, which are present in the form of diamine-platinum(II) complex compounds, are mentioned in German Laid-Open Specification 37 30 746.

A considerable number of the most widely varied compounds—i.a., those of steroidal origin and those with a 2-phenylindole skeleton—that act as antiestrqgens and/or suppress estrogen biosynthesis, are disclosed in WO 93/10741.

The compounds of general formula I according to this application are distinguished from the 2-phenylindoles that are already known by novel side chains on the nitrogen atom. This structural modification leads to especially high antiestrogenically active compounds, which have a very high affinity for the estradiol receptor and displace competitive $^3$H-17β-estradiol from the receptor.

Here, mainly those compounds in which $R^{10}$ and $R^{11}$ together form a di-, tri- or tetramethylene bridge and especially an ethano bridge, i.e., benzo[a]carbazoles, are to be emphasized. In comparison to the analogous compounds, in which $R^{10}$ is a methyl group and $R^{11}$ is a hydrogen atom, the benzo[a]carbazoles according to general formula I are distinguished by an even higher affinity for the estrogen receptor and stronger tumor-inhibiting action.

The cytostatic activity of the new compounds (cell structure tests) is higher than the comparable 2-phenylindoles with an acid amide group in the side chain (EP-A 0348 341).

The $IC_{50}$ values for the new compounds lie in the nano-molar range.

At the same time, these are, for the most part, particularly pure antiestrogens (no residual estrogenic action).

Estrogenic effects on the uteri of mice can no longer be demonstrated in vivo. The compounds have an inhibiting effect on the growth of hormone-dependent tumor cells; they especially inhibit the growth of estrogen-dependent human breast neoplasm cells (MCF-7).

The compounds according to the invention thus are suitable for treating estrogen-dependent diseases, for example, prostatic hyperplasia, breast cancer, endometrial carcinoma, anovulatory infertility and melanoma. In addition, they can be used for prophylaxis and treatment of osteoporosis (Black, L. J.; Sato, M.; Rowley, E. R.; Magee, D. E.; Bekele, A.; Williams, D. C.; Cullinan, G. J.; Bendele, R.; Kauffman, R. F.; Bensch, W. R.; Frolik, C. A.; Termine, J. D. and Bruant, H. U.: Raloxifene [LY 139481 HCl] Prevents Bone Loss and Reduces Serum Cholesterol without Causing Uterine Hypertrophy in Ovariectomized Rats; J. Clin. Invest. 93: 63–69, 1994).

The following pharmacological tests show the action of the compounds according to the invention.

Table 1 shows an overview of the tested compounds of general formula I and their relative binding affinities (RBA*) for the estrogen receptor consisting of calf uteri, compared to 17β-estradiol=100.

The test arrangement is described in Cancer Treatment Reviews 1984, 11, 147.

Table 1 indicates especially the bridge of skeleton atoms 3 and 2', which with an ethano bridge (carbazoles) again ensures significantly increased activities in comparison to the phenylindoles.

Table 2 shows the results of the studies on the cytostatic activity of selected compounds in comparison to tamoxifen.

A strong inhibition of cell growth was found with hormone-sensitive human MCF-7 breast cancer cells.

Compound no. 3 does not show any estrogenic action on the uterus of infantile mice; at a dose of 35 mg/kg, the dry weight of the uterus still lies below the control level. At 10 mg/kg, the action of estrogen (0.4 μg/animal) is completely cancelled out. For compounds nos. 3 and 11, virtually identical results were obtained. The dose/animal was administered s.c., dissolved in olive oil, on three successive days. The dry weight of the uterus [mg]/body weight [g]×100 was determined 24 hours after the last injection. This test is described in detail in Cancer Treatment Reviews, 1984, 11, 147 and J. Med. Chem., 1984, 27, 1439.

TABLE 1

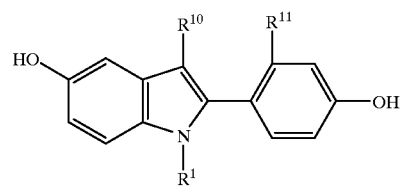

Compounds Nos. 1 to 15: $R^{10} = CH_3$, $R^{11} = H$
Compounds Nos. 16 and 17: $R^{10} + R^{11} = -CH_2-CH_2-$

| No. | Side Chain ($R^1 =$) | RBA(*) |
|---|---|---|
| 1 | $-(CH_2)_{10}-S-(CH_2)_4CH_3$ | 0.3 |
| 2 | $-(CH_2)_{10}-SO-(CH_2)_4CH_3$ | 3.4 |

TABLE 1-continued

Compounds Nos. 1 to 15: $R^{10} = CH_3$, $R^{11} = H$
Compounds Nos. 16 and 17: $R^{10} + R^{11} = -CH_2-CH_2-$

| No. | Side Chain ($R^1 =$) | RBA(*) |
|---|---|---|
| 3 | $-(CH_2)_{10}-SO_2-(CH_2)_4CH_3$ | 4.7 |
| 4 | $-(CH_2)_{12}-SO_2-(CH_2)_2CH_3$ | 1.9 |
| 5 | $-(CH_2)_{12}-SO-(CH_2)_2CH_3$ | 2.9 |
| 6 | $-(CH_2)_8-S-(2-pyridinyl)$ | 1.4 |
| 7 | $-(CH_2)_{10}-S-[2-(N-methyl))\ imidazolyl]$ | 2.0 |
| 8 | $-(CH_2)_{11}-N(-CH_3)-SO_2-(CH_2)_2CH_3$ | 1.8 |
| 9 | $-(CH_2)_{11}-N(-CH_3)-SO_2-CH_2-phenyl$ | 1.0 |
| 10 | $-(CH_2)_{10}-SO_2-N(-CH_3)-(CH_2)_3CH_3$ | 2.6 |
| 11 | $-(CH_2)_9-SO-(CH_2)_3C_2F_5$ | 2.4 |
| 12 | $-(CH_2)_9-SO_2-(CH_2)_3C_2F_5$ | 1.0 |
| 13 | $-(CH_2)_6-S-(CH_2)_3-CON(-CH_3)-(CH_2)_3CH_3$ | 1.3 |
| 14 | $-(CH_2)_{10}-S-CH_2-CO-N(-CH_3)-CH(CH_3)_2$ | 1.7 |
| 15 | $-CH_2-p-C_6H_4-O-(CH_2)_4-SO_2-C_5H_{11}$ | 9.5 |
| 16 | $-(CH_2)_{10}-S-(CH_2)_4CH_3$ | 0.13 |
| 17 | $-(CH_2)_{10}-SO_2-(CH_2)_4CH_3$ | 1.8 |

(*)Determination of the relative binding affinities for the estrogen receptor consisting of calf uterus cytosol. RBA (17β-estradiol) = 100

TABLE 2

| Compound No. | T/C [%] (*) | | | | | |
|---|---|---|---|---|---|---|
| | $1 \cdot 10^{-5}$ M () | $6 \cdot 10^{-6}$ M () | $1 \cdot 10^{-6}$ M () | $1 \cdot 10^{-7}$ M () | $1 \cdot 10^{-8}$ M () | $1 \cdot 10^{-9}$ M () |
| 1 | | | | | | |
| 2 | | | | | | |
| 4 | | | | | | |
| 5 | | | | | | |
| 6 | | | | | | |
| 7 | | | | | | |
| 8 | | | | | | |
| 9 | | | | | | |
| 10 | | | | | | |
| 11 | | | | | | |
| 12 | | | | | | |
| 13 | | | | | | |
| 14 | | | | | | |
| 15 | | | | | | |
| 16 | | | | | | |
| 17 | | | | | | |

TABLE 2-continued tam-
oxi-
fen (*) The T/C values correspond to the quotients of the measured and corrected optical densities from test group. (T) and control group (C); mean value from 16 individual determinations; standard deviation by calculation of errors according to GAUSS.
(**) Substance concentration [mol/l] in the incubation medium

| | T/C [%] (*) | | | | | |
|---|---|---|---|---|---|---|
| Verb.* No. | $1 \cdot 10^{-5}$ M () | $6 \cdot 10^{-6}$ M () | $1 \cdot 10^{-6}$ M () | $1 \cdot 10^{-7}$ M () | $1 \cdot 10^{-8}$ M () | $1 \cdot 10^{-9}$ M () |
| 1 | | | −1.7 ± 8.4 | 21.0 ± 5.2 | 73.5 ± 16.9 | 104.6 ± 18.6 |
| 2 | | | −8.3 ± 12.6 | −16.4 ± 4.8 | −9.4 ± 3.8 | 65.2 ± 18.9 |
| 3 | | | 0.1 ± 6.1 | 3.7 ± 6.2 | 19.1 ± 8.3 | 62.3 ± 12.5 |
| 4 | | | 23.0 ± 7.2 | 32.1 ± 7.5 | 71.0 ± 15.2 | 81.1 ± 19.7 |
| 5 | | | 22.2 ± 12.9 | 37.8 ± 10.1 | 81.8 ± 20.3 | 91.7 ± 20.7 |
| 6 | | | 86.5 ± 15.7 | 92.4 ± 15.8 | 95.7 ± 18.6 | 100.3 ± 16.8 |
| 7 | | | 36.8 ± 8.7 | 60.4 ± 9.1 | 83.8 ± 11.3 | |
| 8 | | | 29.8 ± 14.0 | 56.0 ± 17.6 | 87.4 ± 23.0 | 85.0 ± 25.7 |
| 9 | | | 21.2 ± 8.7 | 39.8 ± 7.8 | 86.4 ± 15.6 | 91.7 ± 21.3 |
| 10 | | | −12.3 ± 6.3 | −13.4 ± 4.5 | 0.5 ± 6.3 | 86.3 ± 18.0 |
| 11 | | | −14.5 ± 4.0 | −10.8 ± 5.0 | −10.4 ± 4.6 | 38.2 ± 17.0 |
| 12 | | | −9.4 ± 4.9 | −11.1 ± 2.8 | −7.5 ± 3.8 | 66.6 ± 16.9 |
| 13 | | | 15.8 ± 6.9 | 40.2 ± 11.4 | 92.9 ± 15.2 | 85.6 ± 16.0 |
| 14 | | | 14.7 ± 8.1 | 20.5 ± 4.8 | 71.6 ± 12.2 | |
| 15 | | | | 14.3 ± 3.5 | 20.9 ± 4.8 | 74.4 ± 5.2 |
| 16 | −38.6 ± 13.9 | −31.1 ± 10.0 | −7.8 ± 8.9 | −18.5 ± 15.4 | | |
| 17 | −32.0 ± 10.1 | −27.1 ± 7.6 | −16.8 ± 5.6 | 0.6 ± 10.7 | | |
| Tamo-xifen | −37.2 ± 8.9 | 2.5 ± 6.0 | 19.5 ± 9.3 | 40.7 ± 14.6 | | |

(*) Die T/C-Werte entsprechen dem Quotienten der gemessenen und korrigierten opdachen Dichten aus Test-(T) und Kontrollguppe (C); Mittelwert aus 16 Einzelbestimmungen; Standardabweichung durch Fehlerberecgnunh nach GAUSS.
(**) Substanzkonxentration [mol/l] im Inkubationsmedium The invention also relates to pharmaceutical preparations that contain at least one compound of general formula I and the use of this compound for treating estrogen-dependent diseases and tumors.

The compounds according to the invention are suitable for the production of pharmaceutical compositions and preparations. The pharmaceutical compositions or pharmaceutical agents contain as active ingredient one or more of the compounds according to the invention, optionally mixed with other pharmacologically or pharmaceutically active substances. The production of the pharmaceutical agents is carried out in a known way, whereby the known and commonly used pharmaceutical adjuvants as well as other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), pages 918 ff; H. v. Czetsch-Lindenwald, Hilfsstoffe für Pharmazie und angrenzende Gebiete [Adjuvants for Pharmaceutics and Related Fields]; Pharm. Ind. No. 2, 1961, pages 72 ff.; Dr. H. P. Fiedler, Lexikon der Hilfsstoffe für Pharmazie, Kosmetik und angrenzende Gebiete [Dictionary of Adjuvants for Pharmaceutics, Cosmetics and Related Fields], Cantor Kg. Aulendorf in Württemberg 1971.

The compounds can be administered orally or parenterally, for example intraperitoneally, intramuscularly, subcutaneously or percutaneously. The compounds can also be implanted in the tissue. The amount of compounds to be administered varies within a wide range and can cover any effective amount. On the basis of the condition to be treated and the type of administration, the amount of compound that is administered is 0.01–20 mg/kg of body weight, preferably 0.1–5 mg/kg of body weight per day.

For oral administration, capsules, pills, tablets, coated tablets, etc. are suitable. In addition to the active ingredient, the dosage units can contain a pharmaceutically compatible vehicle, such as, for example, starch, sugar, sorbitol, gelatin, lubricant, silicic acid, talc, etc. The individual dosage units for oral administration can contain, for example, 10 to 100 mg of active ingredient.

For parenteral administration, the active ingredients can be dissolved or suspended in a physiologically compatible diluent. As a diluent, very frequently oils are used with or without the addition of a solubilizer, a surfactant, a suspending agent or emulsifying agent. Examples of oils that are used are olive oil, peanut oil, cottonseed oil, soybean oil, castor oil and sesame oil.

The compounds can also be used in the form of a depot injection or an implant preparation, which can be formulated such that a delayed release of active ingredient is made possible.

As inert materials, implants can contain, for example, biodegradable polymers or synthetic silicones, such as, for example, silicone rubber. In addition, the active ingredients can be added to, for example, a patch for percutaneous administration.

The production of the compounds according to the invention is carried out as described in the examples. Compounds that are homologous to those in the examples are reproduced by an analogous procedure using corresponding homologous reagents.

The reaction diagram is shown in FIG. 1:

In general, the sulfur-containing side chain, which was obtained according to conventional methods, is (i) introduced directly into the 5-methoxy-2-(4-methoxyphenyl)-3-methylindole by N-alkylation, and (ii) the alkyl ether (especially methyl ether) is cleaved with, for example, boron tribromicle.

Since the sulfoxides decompose under the conditions of ether cleavage, in this case first (viii) the alkylether groups of 5-methoxy-2-(4-methoxyphenyl)-3-methylindole are cleaved and the phenolic hydroxy groups are protected with 3,4-dihydro-2H-pyran, and then (ix) the sulfur-containing side chain is introduced by N-alkylation, and (x) the protective groups are cleaved.

The synthesis of compounds can be carried out with a mixed-functional side chain by (ii) N-alkylation of 5-methoxy-2-(4-methoxyphenyl)-3-methylindole with a corresponding $\alpha$, $\omega$-dibromoalkane, then (v) substitution of the terminal halogen by a thiol group with the isoalkylthiouronium salt, (vi) alkylation of thiol with the corresponding $\omega$-bromoalkanoylamide, and (vii) ether cleavage.

The sulfonamides of general formula I are accessible by (i) alkylation of 5-methoxy-2-(4-methoxyphenyl)-3-methylindole with the corresponding $\omega$-bromoalkanoylamide, (iii) reduction of the carbonyl group with lithium aluminum hydride, (iv) reaction of the amine that is obtained with the corresponding alkylsulfonyl chloride in the presence of a base, and (vii) ether cleavage.

The radical $—(CH_2)_m$,phenylene$—X—(CH_2)_n,—S(O)_mR^4$ can be introduced by reaction of 5-methoxy-2-(4-methoxyphenyl)-3-methylindole with p-bromobenzoic acid esters (or p-bromomethyl- or p-bromoethylbenzoic acid esters) in the presence of CuO (Ullmann reaction) and creation of the side chain via the ester group according to known processes.

For $X=NR^6$, a start can be made from the easily accessible 1-(p-nitrophenyl) derivatives, which are reduced to amine. The residual side chain is then introduced in a nucleophilic substitution reaction with halogen compounds, as they are also used for introducing the side chain directly on the indole-nitrogen. The phenol or thiophenol can be produced with diazonium salt, which then is suitable for obtaining -the derivatives with $X=O$ and $X=S$.

If this is ultimately to be a higher alkyl ether of general formula I, radicals $R^2$ and $R^3$ can be obtained as early as in the starting compound. A carbamoyl radical can be established at these points by deprotonation of the phenolic hydroxy groups and reaction with the corresponding carbamic acid chloride (chloroformic acid amides).

Other possible radicals $R^2$ and $R^3$ according to the invention can be obtained starting from the respective phenol according to familiar methods.

The bridged derivatives, in which $R^{10}+R^{11}$ represent a tri- or tetramethylene bridge, can be obtained analogously to the dihydrobenzocarbazoles by the Fischer-indole synthesis of substituted phenylhydrazines with a corresponding benzocyclohept-2-enone or benzocyclooct-2-enone. A double bond in conjugation with the phenyl ring can be introduced by benzyl halogenation, with, e.g., NBS, and dehydrohalogenation.

The examples below are used for a more detailed explanation of this invention.

EXAMPLES

1. Preparation of the 2-phenylindole Parent Substance 1.1. Synthesis of 2-bromo-4'-methoxypropiophenone 0.30 mol of 4'-methoxypropiophenone is dissolved in 230 ml of glacial acetic acid and mixed with 3 drops of 48% HBr solution. In the stirred mixture, 0.30 mol of bromine is now slowly added in drops while being cooled in an ice bath such that the temperature in the flask does not exceed 15° C. The ice bath is removed, and it is stirred for about another 45 minutes in a continuous nitrogen stream to remove the HBR that is produced in the reaction. Then, it is carefully poured onto 300 ml of ice water. The settled precipitate is suctioned off, washed with several portions of water to remove all bromine and dried in a desiccator overnight. The crude product is recrystallized from 96% ethanol.

Colorless crystals; melting point 65–66° C. Yield: 67%; $C_{10}H_{11}BrO_2$ (243.1).

1.2. Preparation of 5-methoxy-2-(4-methoxyphenyl)-3-methylindole 0.38 mol of p-anisidine is added to 75 ml of N,N-dimethylaniline in a 1 liter reaction flask, heated to 170° C. while being stirred and then a solution of 0.18 mol of 2-bromo-4'-methoxypropiophenone in 240 ml of o-xylene is added in drops at this temperature. The strongly foaming mixture is refluxed for another 3 hours. After the solution is cooled, it is poured onto 600 ml of 2N HCl, stirred thoroughly and extracted three times with ethyl acetate. The organic extracts are washed twice each with 2N HCl and water, dried on magnesium sulfate ($MgSO_4$) and liberated of solvent. For purification, the crude product is chromatographed on silica gel 60 with $CH_2Cl_2$ and then recrystallized from 96% ethanol.

Colorless needles; melting point 135–137° C. Yield: 30%; $C_{17}H_{17}NO_2$ (267.3).

2. Preparation of $\omega$-bromoalkylthioether 18.0 mmol of sodium hydride is suspended under nitrogen in 20 ml of absolute DMF, and 15.0 mmol of thiol in 80 ml of absolute DMF is slowly added in drops at room temperature. After the addition is completed, it is stirred for 30 more minutes, the mixture is poured into a dropping funnel while being exposed to continuous nitrogen gassing, and it is slowly allowed to drip into a stirred solution of 60.0 mmol of $\alpha,\omega$-dibromoalkane in 35 ml of absolute DMF. The batch is held at 50–60° C. for two hours, then water is added until excess sodium hydride is completely destroyed. The clear solution is mixed with 100 ml of ethyl acetate. To achieve a phase separation, 150 ml of water is added. The organic phase is separated, the aqueous phase is extracted three times with ethyl acetate, and the combined organic solvents are washed twice with semi-saturated NaCl solution and with water. After drying on $MgSO_4$, the solvent is drawn off in a vacuum.

The purification of the substance mixture is-carried out by chromatography on silica gel 60. The first fraction contains educt, the second contains the desired monosubstituted product and the third contains the disubstituted product.

1-Bromo-10-(pentylthio)-decane

Purification by chromatography on silica gel 60 with $CH_2Cl_2$/petroleum ether, 40–60 (1:4)[1].

Colorless oil; Yield: 50%; $C_{15}H_{31}BrS$ (323.4).

$^1$H-NMR (CDCl$_3$): δ (ppm)=0.61–2.18 (m; 25H; —(CH$_2$)$_8$—, —CH$_2$CH$_3$), 2.37–2.71 (m; 4H; S(CH$_2$—)$_2$), 3.45 (t; $^3$J=7 Hz; 2H; —CH$_2$Br)

1-Bromo-12-(propylthio)-dodecane

Purification by chromatography on silica gel 60 with $CH_2Cl_2$/petroleum ether, 40–60 (1:4)[1].

[1] Since no fluorescence quenching occurs on the TLC plate in the case of the dialkylthioethers, iodine is vapor-deposited on the solventless chromatogram to detect spots.

Colorless oil; Yield: 35%.

$C_{15}H_{31}BrS$ (323.4).

$^1$H-NMR (CDCl$_3$): δ (ppm)=0.67–2.14 (m; 25H; —(CH$_2$)$_{10}$—, —CH$_2$CH$_3$), 2.51 (t; $^3$J=7 Hz; 4H; S(CH$_2$—)$_2$), 3.40 (t; $^3$J=7 Hz; 2H; —CH$_2$Br)

1-Bromo-8-(2-pyridinylthio)-octane

Purification by chromatography on silica gel 60 with $CH_2Cl_2$ as a mobile phase.

Yellowish oil; Yield: 80%; $C_{12}H_{20}BrNS$ (302.3).

$^1$H-NMR (CDCl$_3$): δ (ppm)=1.00–2.24 (m; 12H; —(CH$_2$)$_6$—), 3.15 (t; $^3$J=7 Hz; 2H; —CH$_2$—S—Ar), 3.37 (t; $^3$J=7 Hz; 2H; —CH$_2$Br), 6.70–7.52 (m; 3H; Ar—H), 8.36 (dd; $^3$J=7 Hz, $^4$J=2 Hz; 1H; Ar—H, H$_6$)

3. Oxidation of the Dialkylthioether 3.1 Production of the α-bromo-ω-(alkylsulfinyl)-alkanes 3.22 mmol of the thioether is dissolved in 200 ml of acetone and mixed with 30 ml of methanol. 5.15 mmol of sodium metaperiodate in 50 ml of water is added in drops while being stirred. It is stirred for another 24 hours, and the solvent is then spun in up to about 50 ml. The residue is mixed with 50 ml of semi-concentrated NaCl solution and extracted three times with ethyl acetate. The combined organic phases are washed once with water, dried on MgSO$_4$ and liberated of solvent on a rotary evaporator. The crude product is recrystallized from a little acetone. To optimize yield, it is placed in a refrigerator (−18° C.) overnight.

1-Bromo-10-(pentylsulfinyl)-decane

White needles; melting point 50–51° C. Yield: 45%; $C_{15}H_{31}BrOS$ (339.4).

1-Bromo-12-(propylsulfinyl)-dodecane

Colorless crystals; melting point 53–54° C. Yield: 51%; $C_{15}H_{31}BrOS$ (339.4).

3.2 Synthesis of α-bromo-ω-(alkylsulfonyl)-alkanes

Variant A: 7.48 mmol of m-chloroperbenzoic acid in 60 ml of chloroform is slowly added in drops to a stirred solution of 3.48 mmol of the dialkylthioether in 170 ml of chloroform.

Variant B: 5.30 mmol of m-chloroperbenzoic acid in 60 ml of chloroform is slowly added in drops to a stirred solution of 3.48 mmol of the dialkylsulfoxide in 150 ml of chloroform.

The batch is stirred for three hours at room temperature and then poured onto 200 ml of saturated NaHCO$_3$ solution and stirred thoroughly for 15 minutes. After being stirred thoroughly for a. short time, the organic phase is separated, the latter is washed with 80 ml of water, dried on MgSO$_4$ and the solvent is spun off. The crude substance is recrystallized from 99% ethanol.

1-Bromo-10-(pentylsulfonyl)-decane

Variant A; colorless fine crystals; melting point 67–68° C. Yield: 70%; $C_{15}H_{31}BrO_2S$ (355.4).

1-Bromo-12-(propylsulfonyl)-dodecane

Variant A; colorless crystals; melting point 65–66° C. Yield: 92%; $C_{15}H_{31}BrO_2S$ (355.4).

1-Bromo-9-(4,4,5,5,5-pentafluoropentylsulfonyl)-nonane

Variant B; colorless needles; melting point 84–85° C. Yield: 87%; $C_{14}H_{24}BrF_5O_2S$ (431.3).

4. Preparation of 1-bromo-10-(n-butyl-methylsulfamoyl)-decane 4.1. Synthesis of 1-bromo-10-mercaptodecane 75.0 mmol of dibromodecane and 50.0 mmol of thiourea are partially dissolved in 50 ml of 96% ethanol and refluxed for a total of 20 hours. Then, 3.0 g of NaOH pellets, dissolved in 60 ml of water, is added to the batch, and it is heated under reflux for another three hours. It is allowed to stand for one hour and the underlying phase that has now precipitated out in oily form is then taken up with a Pasteur pipette. Concentrated H$_2$SO$_4$ is added drop by drop to the upper phase until acid reaction is achieved, and the concentrated H$_2$SO$_4$ is extracted twice with CH$_2$Cl$_2$. The extracts are combined with the oil that has already been taken up, washed once each with water and semi-saturated NaCl solution, dried on MgSO$_4$ and liberated of solvent in a vacuum.

To separate unreacted educt and by-products, the crude batch is chromatographed on silica gel 60 with petroleum ether, 40–60/CH$_2$Cl$_2$ (4:1). The detection of the thiol-containing fractions is carried out by spraying the solventless chromatogram with 3% nitroprusside sodium solution in 1 M of KOH. In this case, substances that contain mercapto groups appear on the chromatogram as red spots on a yellow background.

Colorless oil; Yield: 30%; $C_{10}H_{21}BrS$ (253.2).

$^1$H-NMR (CDCl$_3$): δ (ppm)=0.72–2.16 (m; 16H; —(CH$_2$)$_8$—), 2.21–2.80 (m; 2H; —CH$_2$S—), 3.45 (t; $^3$J=7 Hz; 2H; —CH$_2$Br)

4.2 Preparation of 1-bromo-10-decanesulfonylchlorilde 2.84 mmol of lead(II)-acetate-trihydrate, in 9 ml of 50% ethanol, is dissolved in a reaction flask while being stirred, and a solution, produced from 5.25 mmol of 1-bromo-10-mercaptodecane in 7 ml of 96% ethanol and 1 ml of diethyl ether, is allowed to slowly flow in. The thick precipitate that is produced in this case is stirred vigorously once more for a short time and then suctioned off as completely as possible. The filter cake is suspended first in 10 ml of water, then in 7 ml of acetone, in each case suctioned off again and dried overnight in a desiccator on blue gel.

The dried mercaptide is put into 10 ml of a 65% HNO$_3$ solution while being stirred at room temperature. After about an hour, the NO$_x$ formation is completed, and the solution is completely bleached. The batch is then put into an ice bath and diluted with 30 ml of ice water. The mixture is left in the ice bath for another 15 minutes, the paste that has become stiff is suctioned off, resuspended again first in 30 ml of ice water, then in 10 ml of acetone and in each case suctioned off again. The product is dried again overnight in a desiccator.

The white, lumpy solid is intimately mixed in a reaction flask with 10.5 mmol of phosphorus pentachloride and heated for 2.5 hours at 80° C. Then, the batch is allowed to cool, it is placed on ice and quickly mixed with 100 ml of ice water. After the mixture was stirred thoroughly for 15 minutes, it is extracted three times with diethyl ether, the organic extracts are washed twice with water, dried on $MgSO_4$ and the solvent is spun off.

Brown oil; Yield: 43%; $C_{10}H_{20}BrClO_2S$ (319.7).

$^1$H-NMR ($CDCl_3$): δ (ppm)=0.73–2.22 (m; 16H; —$(CH_2)_8$—,), 3.40 (t; $^3$J=7 Hz; 2H; —$CH_2Br$), 3.48–3.84 (m; 2H; —$CH_2SO_2Cl$)

4.3. Preparation of 1-bromo-10-(n-butyl-methylsulfamoyl)-decane 9.63 mmol of n-butylmethylamine is dissolved in 6 ml of absolute $CH_2Cl_2$. In a moisture-free environment, 1.85 mmol of 1-bromo-10-decanesulfonyl chloride is now slowly added in drops to 2.5 ml of $CH_2Cl_2$ while being cooled with ice. Then, it is stirred for another five hours at room temperature. The mixture is mixed with 10 ml of water, stirred thoroughly for a short time and the organic phase is separated. The aqueous phase is extracted with ether, and the combined organic phases are then washed with saturated NaCl solution and water. After drying on $MgSO_4$, the solvent is removed in a rotary evaporator.

Brown oil; Yield: 82%; $C_{15}H_{32}BrNO_2S$ (370.4).

$^1$H-NMR ($CDCl_3$): δ (ppm)=0.69–2.14 (m; 23H; —$(CH_2)_8$—, —$(CH_2)_2CH_3$), 2.73–3.28 (m; 4H; —$CH_2SO_2$—N—$CH_2$—), 2.88 (s; 3H; —$SO_2$—N—$CH_3$), 3.44 (t; $^3$J=7 Hz; 2H; —$CH_2Br$)

5. Introduction of Substituted Side Chains in 5-methoxy-2-(4-methoxyphenyl)-3-methylindole 18.0 mmol of sodium hydride is suspended in 20 ml of absolute DMF under nitrogen and while being cooled in an ice bath. After 15 minutes, 13.0 mmol of 5-methoxy-2-(4-methoxyphenyl)-3-methylindole in 75 ml of absolute DMF is added in drops while being cooled continuously. The mixture is stirred until no more gas generation can be detected (about 30 minutes).

Then, a solution of 13.0 mmol of the bromoalkane derivative in 60 ml of absolute DMF is added in drops, the ice bath is removed and stirred for another two hours at room temperature. By carefully adding water in drops, excess sodium hydride is destroyed, and it is mixed with 100 ml of ethyl acetate and 250 ml of water. The organic phase is separated, and the aqueous phase is shaken out three times with ethyl acetate. The combined. organic phases are washed three times with water, dried on $MgSO_4$ and the solvent is spun off.

Example 1

5-Methoxy-2-(4-methoxyphenyl)-3-methyl-1-[10-(pentylthio)-decyl]-indole

Purification is carried out by chromatography on silica gel 60 with $CH_2Cl_2$/petroleum ether, 40–60 (2:1) as a mobile phase.

Greenish oil; Yield: 91%; $C_{32}H_{47}NO_2S$ (509.8).

$^1$H-NMR ($CDCl_3$): δ (ppm)=0.70–1.94 (m; 25H; —$(CH_2)_8$—, —$(CH_2)_3CH_3$), 2.19 (s; 3H; Ar—$CH_3$), 2.32–2.64 (m; 4H; $S(CH_2$—$)_2$), 3.85 (s; 6H; —$OCH_3$), 3.91 (t; $^3$J=7 Hz; 2H; ArN—$CH_2$—), 6.60–7.33 (m; 7H; Ar—H)

Example 2

5-Methoxy-2-(4-methoxyphenyl)-3-methyl-1-[10-(pentylsulfonyl)-decyl]-indole

Purification by chromatography on silica gel 60. To elute the two preliminary fractions, $CH_2Cl_2$ is used as a mobile phase; to isolate the product, $CH_2Cl_2$/ethyl acetate (30:1) is used.

Colorless, waxy solid; Yield: 92%; $C_{32}H_{47}NO_4S$ (541.8).

$^1$H-NMR ($CDCl_3$): δ (ppm)=0.72–2.15 (m; 25H; —$(CH_2)_8$—, —$(CH_2)_3CH_3$), 2.20 (s; 3H; Ar—$CH_3$), 2.75–3.16 (m; 4H; $SO_2(CH_2$—$)_2$), 3.88 (s; 6H; —$OCH_3$), 3.97 (t; $^3$J=7 Hz; 2H; ArN—$CH_2$—), 6.69–7.45 (m; 7H; Ar—H)

Example 3

5-Methoxy-2-(4-methoxyphenyl)-3-methyl-1-[12-(propylsulfonyl)-dodecyl]-indole

Purification by chromatography on silica gel 60. To elute the preliminary phase, $CH_2Cl_2$ is used as a mobile phase; to isolate the product, $CH_2Cl_2$/ethyl acetate (6:1) is used.

Yellowish oil; Yield: 92%; $C_{32}H_{47}NO_4S$ (541.8).

$^1$H-NMR ($CDCl_3$): δ (ppm)=0.83–2.25 (m; 25H; —$(CH_2)_{10}$—, —$CH_2CH_3$), 2.30 (s; 3H; Ar—$CH_3$), 2.83–3.17 (m; 4H; $SO_2(CH_2$—$)_2$), 4.01 (s; 6H; —$OCH_3$), 4.08 (t; $^3$J=7 Hz; 2H; ArN—$CH_2$—), 6.73–7.35 (m; 7H; Ar—H)

Example 4

5-Methoxy-2-(4-methoxyphenyl)-3-methyl-1-[9-(4,4,5,5,5-pentafluoropentylsulfonyl)-nonyl]-indole Purification by chromatography on silica gel 60 with $CH_2Cl_2$/ethyl acetate (40:1) as an eluent and subsequent recrystallization from n-hexane.

Colorless needles; melting point 87.5–89° C. Yield: 58%; $C_{31}H_{40}F_5NO_4S$ (617.7).

Example 5

1-[10-(n-Butyl-methylsulfamoyl)-decyl]-5-methoxy-2-(4-methoxyphenyl)-3-methylindole Purification by chromatography on silica gel 60 with $CH_2Cl_2$/ethyl acetate (50:1) as a mobile phase.

Colorless oil; Yield: 23%; $C_{32}H_{48}N_2O_4S$ (556.8).

$^1$H-NMR ($CDCl_3$): δ (ppm)=0.75–2.12 (m; 23H; —$(CH_2)_8$—, —$(CH_2)_2CH_3$), 2.21 (s; 3H; Ar—$CH_3$), 2.73–3.33 (m; 4H; —$CH_2SO_2$—N—$CH_2$—), 2.86 (s; 3H; —$SO_2$—N—$CH_3$), 3.91 (s; 6H; —$OCH_3$), 3.99 (t; $^3$J=7 Hz; 2H; ArN—$CH_2$—), 6.78–7.48 (m; 7H; Ar—H)

Example 6

5-Methoxy-2-(4-methoxyphenyl)-3-methyl-1-[8-(2-pyridinylthio)-octyl]-indole

Purification by chromatography on silica gel 60 with $CH_2Cl_2$ as an eluent and subsequent recrystallization from n-hexane.

Yellowish, prism-like crystals; melting point 75–77° C. Yield (after chromatography): 86%; $C_{30}H_{36}N_2O_2S$ (488.7).

Example 7

5-Methoxy-2-(4-methoxyphenyl)-3-methyl-1-[10-(N-methylcarbamoyl)-decyl]-indole

Purification by recrystallization from n-hexane/ether (1:1)

Colorless needles; melting point 88° C. Yield: 75%; $C_{29}H_{40}N_2O_3$ (464.6).

6. Preparation of 5-methoxy-2-(4-methoxyphenyl)-3-methyl-1-[ω-(N-methylalkylsulfonamido)-alkyl]-indole 6.1 Reduction of 5-methoxy-2-(4-methoxyphenyl)-3-methyl-1-[10-(N-methyl-carbamoyl)-decyl]-indole 25.8 mmol of lithium aluminum hydride is weighed into a reaction flask, suspended in 150 ml of absolute THF while being exposed to nitrogen gassing and heated to boiling in a water bath. While being heated, 10.3 mmol of methoxyindole is then slowly added in drops to 250 ml of absolute THF such that the batch does not foam too much but continues to reflux. After the addition is completed, it is boiled for another hour, the water bath is then removed and the mixture is allowed to stir overnight at room temperature. Excess lithium alanate is then destroyed by slowly adding in drops a total of 40 ml of water. The amorphous white precipitate that is produced in this case is suctioned off. The filtrate is liberated of THF as completely as possible by spinning off, and the residue is extracted three times with ethyl acetate; the filter cake is suspended again in ethyl acetate and again suctioned off. The combined organic phases are washed twice with water, dried on $MgSO_4$, and the solvent is removed in a vacuum.

The purification is carried out by chromatography on silica gel 60. Preliminary fractions that contain by-products are eluted with ethyl acetate; the product 5-methoxy-2-(4-methoxyphenyl)-3-methyl-1-[11-(methylamino)-undecyl]-indole is then obtained by changing the mobile solvent (methanol/triethylamine, 3:1).

Yellow, cloudy oil; Yield: 77%; $C_{29}H_{42}N_2O_2$ (450.7).

$^1$H-NMR (CDCl$_3$): δ (ppm)=0.82–1.80 (m; 18H; —(CH$_2$)$_9$—), 2.17 (s; 3H; Ar—CH$_3$), 2.28–2.70 (m; 2H; —CH$_2$—N=), 2.40 (s; 3H; =N—CH$_3$), 3.85 (s; 6H; —OCH$_3$), 3.92 (t; $^3$J=7 Hz; 2H; ArN—CH$_2$—), 6.69–7.39 (m; 7H; Ar—H)

6.2 Reaction of 5-methoxy-2-(4-methoxyphenyl)-3-methyl-1-[11-(methylamino)-undecyl]-indole with Sulfonic Acid Chlorides 3.48 mmol of the indole is dissolved in 30 ml of absolute chloroform, mixed with 10 ml of triethylamine and cooled in an ice bath while being stirred. Then, 34.8 mmol of acid chloride is slowly added in drops to 18 ml of absolute chloroform, such that the temperature of the batch does not exceed 20° C. Then, the ice bath is removed, and stirring is continued at room temperature. Alkylsulfonic acid chlorides have proven very reactive: the reaction can be completed after two hours; the phenylmethanesulfonic acid chloride behaves far more inertly, therefore it is heated at 40° C. for five hours in this case, and the batch is then stirred overnight at room temperature. For working-up, 150 ml of ethyl acetate and 100 ml of CH$_2$Cl$_2$ are added to the batch, and the mixture is shaken out twice with saturated NaHCO$_3$ solution. After the organic phase is dried on MgSO$_4$, it is liberated of solvent in a vacuum.

The crude products are purified by column chromatography, whereby strongly colored viscous oils are obtained. The coloring is not destroyed in the case of further reaction (ether cleavage) and can be separated by column chromatography in this step by the then more polar eluent.

Example 8

5-Methoxy-2-(4-methoxyphenyl)-3-methyl-1-[11-(N-methyl-propylsulfonamido)-undecyl]-indole Purification by chromatography on silica gel 60 with CH$_2$Cl$_2$/ethyl acetate (50:1) as an eluent.

Dark red oil; Yield: 86%; $C_{32}H_{48}N_2O_4S$ (556.8).

$^1$H-NMR (CDCl$_3$): δ (ppm)=0.75–2.11 (m; 23H; —(CH$_2$)$_9$—, —CH$_2$CH$_3$), 2.20 (s; 3H; Ar—CH$_3$), 2.63–3.43 (m; 4H; —CH$_2$—NSO$_2$—CH$_2$—), 2.87 (s; 3H; =N—CH$_3$), 3.91 (s; 6H; —OCH$_3$), 3.97 (t; $^3$J=7 Hz; 2H; ArN—CH$_2$—), 6.78–7.47 (m; 7H; Ar—H)

Example 9

5-Methoxy-2-(4-methoxyphenyl)-3-methyl-1-[11-(N-methyl-phenylmethanesulfonamido)-undecyl]-indole Purification by chromatography on silica gel 60. The preliminary fractions are flushed from the column with CH$_2$Cl$_2$; the product is then eluted with the mobile solvent CH$_2$Cl$_2$/ethyl acetate (10:1).

Orange, viscous oil; Yield: 39%; $C_{36}H_{48}N_2O_4S$ (604.9).

$^1$H-NMR (CDCl$_3$): δ (ppm)=0.85–1.74 (m; 18H; —(CH$_2$)$_9$—), 2.18 (s; 3H; Ar—CH$_3$), 2.67 (s; 3H; =N—CH$_3$), 2.93 (t; $^3$J=7 Hz; 2H; —CH$_2$—N=), 3.86 (s; 6H; —OCH$_3$), 3.95 (t; $^3$J=7 Hz; 2H, ArN—CH$_2$—), 4.20 (s; 2H; —SO$_2$—CH$_2$—Ar), 6.71–7.43 (m; 7H; Ar—H, indole), 7.33 (s; 5H; Ar—H, phenyl)

7. Preparation of 2-phenylindole Derivatives with a Mixed-functional Side Chain 7.1 General Instructions for the Preparation of N,N-disubstituted Bromoalkanoylamides 45.0 mmol of the secondary amine is dissolved in 60 ml of absolute methylene chloride. In a moisture-free environment, 20.0 mmol of the bromoalkanoyl chloride is now slowly added in drops while being cooled in an ice bath, such that the temperature of the batch does not exceed 20° C. Then, it is stirred overnight at room temperature. The mixture is mixed with 50 ml of water and stirred thoroughly for a short time. The organic phase is separated, and the aqueous phase is extracted with 30 ml of ether. The combined organic phases are washed with saturated NaCl solution and water. After drying on MgSO$_4$, the solvent is removed in a rotary evaporator.

N-(4-Bromobutanoyl)-(n-butyl)-methylamine

Purification by distillation; oil that turns yellow over time; boiling point 114–116° C., 0.1 torr Yield: 18%; $C_{12}H_{22}BrClO$ (297.7).

$^1$H-NMR (CDCl$_3$): δ (ppm)=0.70–1.83 (m; 7H; —(CH$_2$)$_2$CH$_3$), 1.93–2.69 (m; 4H; —(CH$_2$)$_2$CO—), 2.91 (s), 2.97 (s; 3H; —CON(CH$_3$)—), 3.11–3.50 (m; 2H; —CON(CH$_2$—)—), 3.64 (t; $^3$J=6 Hz; 2H; —CH$_2$Br)

7.2 Synthesis of 1-(6-bromohexyl)-5-methoxy-2-(4-methoxyphenyl)-3-methylindole

Synthesis is performed basically analogously to 5., but with the following changes: the dibromohexane that is used in 4× excess is dissolved in a second reaction flask also while being exposed to nitrogen gassing and while being stirred in an ice bath, and then the indole-sodium salt that is dissolved in DMF is allowed to quickly flow in. The mixture is stirred for two hours at room temperature and then worked up as described under item 5.

The purification of the crude product is carried out by chromatography on silica gel 60 with petroleum ether, 40–60/ethyl acetate (5:1) as a mobile phase.

Colorless oil; Yield: 81%; $C_{23}H_{28}BrNO_2$ (430.4).

$^1$H-NMR (CDCl$_3$): δ (ppm)=0.92–1.92 (m; 8H; —(CH$_2$)$_4$—), 2.18 (s; 3H; Ar—CH$_3$), 3.24 (t; $^3$J=7 Hz; 2H; —CH$_2$Br), 3.85 (s; 6H; —OCH$_3$), 3.94 (t; $^3$J=7 Hz; ArN—CH$_2$—), 6.68–7.36 (m; 7H; Ar—H)

Example 10

7.3 Preparation of 1-(6-Mercaptohexyl)-5-methoxy-2-(4-methoxyphenyl)-3-methylindole The synthesis is performed analogously to 4.1 with the following changes: 5.55 mmol of the product that is produced under 9.2 is dissolved together with 16.7 mmol of thiourea in 75 ml of absolute THF and refluxed for 20 hours. For cleavage of the isothiouronium salt, 4.4 g of NaOH is added to 75 ml of water, and the subsequent procedure is as described under 4.1.

The purification of the crude product is carried out by chromatography on silica gel 60 with $CH_2Cl_2$/petroleum ether, 40–60 (3:1) as an eluent.

Yellowish oil; Yield: 69%; $C_{23}H_{29}NO_2S$ (383.6).

$^1$H-NMR (CDCl$_3$): δ (ppm)=0.94–1.78 (m; 8H; —(CH$_2$)$_4$—), 2.20 (s; 3H; Ar—CH$_3$), 2.19–2.63 (m; 2H; —CH$_2$—SH), 3.87 (s; 6H; —OCH$_3$), 3.98 (t; $^3$J=7 Hz; ArN—CH$_2$—), 6.74–7.46 (m; 7H; Ar—H)

Example 11

7.4. Preparation of 1-{6-[3'-(n-butyl-methylcarbamoyl)-propylthio]-hexyl}-5-methoxy-2-(4-methoxyphenyl)-3-methylindole Execution is analogous to 2.

The batch is purified by chromatography on silica gel 60 with $CH_2Cl_2$/ethyl acetate (4:1) as a mobile phase.

Colorless oil; Yield: 93%; $C_{32}H_{46}N_2O_3S$ (538.8).

$^1$H-NMR (CDCl$_3$): δ (ppm)=0.69–2.71 (m; 23H; —(CH$_2$)$_5$S(CH$_2$)$_3$CON—, —(CH$_2$)$_2$CH$_3$), 2.20 (s; 3H; Ar—CH$_3$), 2.90, 2.94 (s; 3H; —CON(CH$_3$)—), 3.09–3.60 (m; 2H; —CON(CH$_2$—)—), 3.88 (s; 6H; —OCH$_3$), 3.98 (t; $^3$J=7 Hz; ArN—CH$_2$—), 6.76–7.48 (m; 7H; Ar—H)

8. Ether Cleavage of 1-substituted 5-methoxy-2-(4-methoxyphenyl)-3-methylindoles 30.0 mmol of boron tribromide in 120 ml of absolute methylene chloride is introduced in an ice/common salt bath under nitrogen. 7.50 mmol of 1-substituted 5-methoxy-2-(4-methoxyphenyl)-3-methylindole in 120 ml of absolute methylene chloride is slowly added in drops to it. Then, the batch is allowed to reach room temperature, and it is stirred for another three hours. While being cooled with ice, it is first carefully mixed, later in larger portions with a total of 170 ml of saturated NaHCO$_3$ solution, and it is stirred vigorously, until no more gas generation can be detected. The lumps that adhere to the glass wall dissolve at the latest after ethyl acetate is added and while the mixture is being stirred vigorously. The organic phase is separated, the aqueous phase is extracted twice more with ethyl acetate, and the combined solvents are washed once each with saturated NaHCO$_3$ solution and water. After drying on MgSO$_4$, the solvent is spun off.

Example 12

5-Hydroxy-2-(4-hydroxyphenyl)-3-methyl-1-[10-(pentylthio)-decyl]-indole (1)

Purification by chromatography on silica gel 60. To remove the preliminary fractions, it is eluted with $CH_2Cl_2$/ethyl acetate (50:1), then a switch is made to the mobile solvent mixture of $CH_2Cl_2$/ethyl acetate (10:1).

Yellow oil, which slowly crystallizes out; Yield: 81%; $C_{30}H_{43}NO_2S$ (481.7).

$^1$H-NMR (CDCl$_3$): δ (ppm)=0.68–1.90 (m; 25H; —(CH$_2$)$_8$—, —(CH$_2$)$_3$CH$_3$), 2.16 (s; 3H; Ar—CH$_3$), 2.37–2.70 (m; 4H; S(CH$_2$—)$_2$), 3.97 (t; $^3$J=7 Hz; 2H; ArN—CH$_2$—), 5.22 (s, br; 2H; —OH), 6.69–7.40 (m; 7H; Ar—H)

Example 13

5-Hydroxy-2-(4-hydroxyphenyl)-3-methyl-1-[10-(pentylsulfonyl)-decyl]-indole (3)

Purification by chromatography on silica gel 60 with $CH_2Cl_2$/ethyl acetate (7:1) as an eluent; after dissolving in CHCl$_3$, the substance slowly crystallizes out at −18° C. over a period of several days.

Colorless fine crystals; melting point 115–117° C. Yield: 64%; $C_{30}H_{43}NO_4S$ (513.7).

Example 14

5-Hydroxy-2-(4-hydroxyphenyl)-3-methyl-1-[12-(propylsulfonyl)-dodecyl]-indole (4)

Purification by chromatography on silica gel 60 with $CH_2Cl_2$/ethyl acetate (7:1) as a mobile phase.

Yellow-white resin; Yield: 76%; $C_{30}H_{43}NO_4S$ (513.7).

$^1$H-NMR (CDCl$_3$): δ (ppm)=0.77–2.12 (m; 25H; —(CH$_2$)$_{10}$—, —CH$_2$CH$_3$), 2.13 (s; 3H; Ar—CH$_3$), 2.76–3.18 (m; 4H; SO$_2$(CH$_2$—)$_2$), 3.95 (t; $^3$J=7 Hz; 2H; ArN—CH$_2$—), 6.66–7.40 (m; 7H; Ar—H)

Example 15

5-Hydroxy-2-(4-hydroxyhenyl)-3-methyl-1-[9-(4,4,5,5,5-pentafluoropentyl)-nonyl]-indole (10)

Purification by chromatography on silica gel 60 with $CH_2Cl_2$/ethyl acetate (6:1) as a mobile solvent.

Greenish resin; Yield: 63%; $C_{29}H_{36}F_5NO_4S$ (589.7).

$^1$H-NMR (CDCl$_3$): δ (ppm)=0.71–2.42 (m; 16H; —(CH$_2$)$_7$—, —CH$_2$—), 1.99–2.34 (m; 2H; —CH$_2$C$_2$F$_5$), 2.13 (s; 3H; Ar—CH$_3$), 2.83–3.28 (m; 4H; SO$_2$(CH$_2$—)$_2$), 3.97 (t; $^3$J=7 Hz; 2H; ArN—CH$_2$—), 4.97 (s, br; 1H; —OH), 6.10 (s, br; 1H; —OH), 6.70–7.41 (m; 7H; Ar—H)

Example 16

5-Hydroxy-2-(4-hydroxyphenyl)-3-methyl-1-[8-(2-pryidinylthio)-octyl]-indole (5)

Purification by chromatography on silica gel 60 with $CH_2Cl_2$/ethyl acetate (7:1) as a mobile solvent.

Greenish foam; melting point 56–60° C.; Yield: 86%; $C_{28}H_{32}N_2O_2S$ (460.6).

Example 17

1-[10-(n-Butyl-methylsulfamoyl)-decyl]-5-hydroxy-(4-hydroxyphenyl)-3-methylindole (8)

Purification by chromatography on silica gel 60 with $CH_2Cl_2$/ethyl acetate (8:1) as a mobile phase.

Greenish resin; Yield: 94%; $C_{30}H_{44}N_2O_4S$ (528.8).

$^1$H-NMR (CDCl$_3$): δ (ppm)=0.66–2.27 (m; 23H; —(CH$_2$)$_8$—, —(CH$_2$)$_2$CH$_3$), 2.14 (s; 3H; Ar—CH$_3$), 2.74–3.33 (m; 4H; —CH$_2$SO$_2$—N—CH$_2$—), 2.88 (s; 3H; —SO$_2$—N—CH$_3$), 3.97 (t; $^3$J=7 Hz; 2H; ArN—CH$_2$—), 5.10 (s, br: 1H; —OH), 6.33 (s, br; 1H; —OH), 6.69–7.40 (m; 7H; Ar—H)

Example 18

5-Hydroxy-2-(4-hydroxyphenyl)-3-methyl-1-[11-(N-methtyl-propylsulfonamido)-undecyl]-indole (6)

Purification by chromatography on silica gel 60 with $CH_2Cl_2$/ethyl acetate (8:1) as an eluent.

Dark-yellow resin; Yield: 75%; $C_{30}H_{44}N_2O_4S$ (528.8).

$^1$H-NMR (CDCl$_3$): δ (ppm)=0.85–2.22 (m; 23H; —(CH$_2$)$_9$—, —CH$_2$CH$_3$), 2.12 (s; 3H; Ar—CH$_3$), 2.74–3.30 (m; 4H; —CH$_2$—NSO$_2$—CH$_2$—), 2.85 (s; 3H; =N—CH$_3$), 3.91 (t; $^3$J=7 Hz; 2H; ArN—CH$_2$—), 4.85 (s, br; 1H; —OH), 6.09 (s, br; 1H; —OH), 6.59–7.28 (m; 7H; Ar—H)

Example 19

5-Hydroxy-2-(4-hydroxyphenyl)-3-methyl-1-[11-(N-methnyl-phenylmethanesulfonamido)-undecyl]-indole (7)

Purification by chromatography on silica gel 60 with CH$_2$Cl$_2$/ethyl acetate (10:1) as a mobile phase.

Viscous, yellow resin; Yield: 62%; $C_{34}H_{44}N_2O_4S$ (576.8).

$^1$H-NMR (CDCl$_3$): δ (ppm)=0.70–1.81 (m; 18H; —(CH$_2$)$_9$—), 2.17 (s; 3H; Ar—CH$_3$), 2.70 (s; 3H; =N—CH$_3$), 2.97 (t; $^3$J=7 Hz; 2H; —CH$_2$—N=), 3.95 (t; $^3$J=7 Hz; 2H; ArN—CH$_2$—), 4.26 (s; 2H; —SO$_2$—CH$_2$—Ar), 4.87 (s, br: 1H; —OH), 6.09 (s, br; 1H; —OH), 6.64–7.50 (m; 7H; Ar—H, indole), 7.38 (s; 5H; Ar—H, phenyl)

Example 20

1-{6-[3'-(n-Butyl-methylcarbamoyl)-propylthio]-hexyl}-5-methoxy-2-(4-methoxyphenyl)-3-methylindole (11)

Purification by chromatography on silica gel 60 with CH$_2$Cl$_2$/ethyl acetate (2:1) as a mobile phase.

Yellowish resin; Yield: 93%; $C_{30}H_{42}N_2O_3S$ (510.7).

$^1$H-NMR (CDCl$_3$): δ (ppm)=0.64–2.77 (m; 23H; —(CH$_2$)$_5$S(CH$_2$)$_3$CON—, —(CH$_2$)$_2$CH$_3$), 2.14 (s; 3H; Ar—CH$_3$), 2.98 (s, br; 3H; —CON(CH$_3$)—), 3.11–3.62 (m; 2H; —CON(CH$_2$—)—), 3.95 (t; $^3$J=7 Hz; 2H; ArN—CH$_2$—), 5.49 (s, br; 1H; —OH), 6.62–7.34 (m; 7H; Ar—H), 8.49 (s, br; 1H; —OH).

9. Preparation of 1-[ω-(alkylsulfinyl)-alkyl]-5-hydroxy-2-(4-hydroxyphenyl)-3-methylindoles 9.1. Ether Cleavage of the N-unsubstituted 2-phenylinidole Parent Substance 340 mmol of boron tribromide in 700 ml of absolute methylene chloride is introduced into an ice/common salt bath under nitrogen. 56.6 mmol of 5-methoxy-2-(4-methoxyphenyl)-3-methylindole in 350 ml of absolute methylene chloride is slowly added in drops to it such that the temperature in the reaction flask does not exceed –4° C. After the addition is completed, the ice bath is removed, it is allowed to reach room temperature while being stirred, and the batch is refluxed for a total of five hours in the water bath, whereby exposure to nitrogen gassing is continued to a very small extent. For hydrolysis of the excess boron tribromide, a total of 800 ml of saturated NaHCO$_3$ solution is added in small portions to the batch while being stirred vigorously in an ice bath. As soon as the vigorous smoke generation ceases and gas generation has dropped off, 300 ml of ethyl acetate is added to the reaction mixture and stirring is continued for another half hour. After the organic phase is separated, the aqueous phase is shaken out several more times, the combined organic extracts are washed with saturated NaHCO$_3$ solution and water, dried on MgSO$_4$, and the solvent is spun off.

The purification of the crude product is carried out by chromatography on silica gel 60 with CH$_2$Cl$_2$/ethyl acetate (3:1). During spinning-in, it is to be noted that the solvent suddenly "deflagrates," in most cases starting at a certain pressure. By taking up the residue in pure CH$_2$Cl$_2$, the product can be obtained as a fine amorphous powder after vigorous stirring and subsequent suctioning-off.

Yellow powder; melting point 201–205° C. (decomposition); Yield: 83%; $C_{15}H_{13}NO_2$ (239.3).

For analytical purposes, in addition a small amount of crystalline substance can be obtained by recrystallization from boiling CHCl$_3$ (solubility: about 3 mg/ml of boiling CHCl$_3$; yield after prolonged standing at –18° C.: 60%).

9.2. Etherification of the Oxygen Groups of 5-hydroxy-2-(4-hydroxyphenyl)-3-methylindole with 3,4-dihydro-2H-pyran 13.1 mmol of 5-hydroxy-2-(4-hydroxyphenyl)-3-methylindole is dissolved in 85 ml of absolute DMF, and 131 mmol of 3,4-dihydro-2H-pyran and 13.1 mmol of pyridinium-(toluene-4-sulfonate) are added to the batch. The mixture is stirred for a total of 70 hours at room temperature. For working-up, two parts by volume of water and one part by volume of ethyl acetate are added, the organic phase is separated, and the aqueous phase is extracted three more times with ethyl acetate. The combined organic phases are washed three times with semi-concentrated NaCl solution, dried on MgSO$_4$ and liberated of solvent in a vacuum.

The separation of by-products of the reaction and monoetherified product is achieved by chromatography on silica gel 60 with CH$_2$Cl$_2$/ethyl acetate (30:1), whereby the diether is eluted as a first fraction from the column. For analytical purposes, a portion of the product is dissolved in a little ethanol, mixed with five parts by volume of n-hexane at boiling heat and recrystallized by slow cooling to –18° C.

White, flocculent powder; melting point 175–178° C. Yield: 38%; $C_{25}H_{29}NO_4$ (407.5).

9.3. Introduction of the Side Chains with a Sulfoxy Group

This alkylation reaction is basically performed analogously to 5. In contrast to this, sodium hydride which, as a reducing agent, can reduce, for example, a sulfoxy group back to a thioether, can now be used in this variant in a minimal amount: 18.0 mmol is suspended in an ice bath in 20 ml of absolute DMF while being exposed to nitrogen gassing. 19.6 mmol of 3-methyl-5-(α-tetrahydropyranyloxy)-2-[4-(α-tetrahydropyranyloxy)-phenyl]-indole is then added in drops to 75 ml of absolute DMF. After stirring is continued in an ice bath (about 30 minutes), the reaction batch must contain no more sodium hydride particles; a clear solution must thus be present, otherwise some indole is added. Then, the solution of 16.4 mmol of the side chain in 60 ml of absolute DMF is added in drops, the ice bath is removed, and it is stirred for 2 more hours at room temperature. The further working-up is carried out analogously to 5.

Example 21

3-Methyl-1-[10-(pentylsulfinyl)-decyl]-5-(a-tetrahydropyranyloxy)-2-[4-(a-tetrahydropyranyloxy)-phenyl]-indole Purification of the product is carried out by chromatography on silica gel 60 with ethyl acetate/methanol (30:1) as a mobile phase.

Greenish fluorescent oil; Yield: 83%; $C_{40}H_{59}NO_5S$ (666.0).

$^1$H-NMR (CDCl$_3$): δ (ppm)=about 0.7–2.4 (m; 37H; —(CH$_2$)$_8$—, —(CH$_2$)$_3$CH$_3$, —(CH$_2$)$_3$—, pyran ring), 2.17 (s; 3H; Ar—CH$_3$), 2.45–2.82 (m; 4H; SO(CH$_2$—)$_2$), 3.33–4.24 (m; 4H; —CH$_2$O—, pyran ring), 3.92 (t; $^3$J=7 Hz; 2H; ArN—CH$_2$—), 5.29–5.55 (m; 2H; —O(CH—)O—), 6.79–7.37 (m; 7H; Ar—H)

Example 22

3-Methyl-1-[12-(propylsulfinyl-dodecyl]-5-(a-tetrahydropyranyloxy)-2-[4-(a-tetrahydropyranyloxy)-phenyl]-indole Purification is carried out by chromatography on silica gel 60 with ethyl acetate/methanol (8:1) as a mobile solvent.

Brownish fluorescent oil; Yield: 90%; $C_{40}H_{59}NO_5S$ (666.0).

$^1$H-NMR (CDCl$_3$): δ (ppm)=about 0.9–2.3 (m; 37H; —(CH$_2$)$_{10}$—, —CH$_2$CH$_3$, —(CH$_2$)$_3$—, pyran ring), 2.16 (s; 3H; Ar—CH$_3$), 2.49–2.81 (m; 4H; SO(CH$_2$—)$_2$), 3.36–4.36 (m; 6H; ArN—CH$_2$—, —CH$_2$O—, pyran ring), 5.32–5.56 (m; 2H; —O(CH—)O—), 6.82–7.39 (m; 7H; Ar—H)

Example 23

3-Methyl-1-[9-(4,4,5,5,5-pentafluoropentylsulfinyl)-nonyl]-5-(a-tetrahydropyranyloxy)-2-[4-(a-tetrahydropyranyloxy)-phenyl]-indole Purification of the product is carried out by chromatography on silica gel 60 with ethyl acetate/methanol (30:1) as an eluent.

Greenish fluorescent oil, which slowly crystallizes out over time

Yield: 86%; $C_{39}H_{52}F_5NO_5S$ (741.9).

$^1$H-NMR (CDCl$_3$): δ (ppm)=about 0.8–2.6 (m; 30H; —(CH$_2$)$_7$—, —(CH$_2$)$_2$C$_2$F$_5$, —(CH$_2$)$_3$—, pyran ring), 2.17 (s; 3H; Ar—CH$_3$), 2.49–2.88 (m; 4H; SO(CH$_2$—)$_2$), 3.33–4.23 (m; 4H; —CH$_2$O—, pyran ring), 3.92 (t; $^3$J=7 Hz; 2H; ArN—CH$_2$—), 5.30–5.54 (m; 2H; —O(CH—)O—), 6.79–7.38 (m; 7H; Ar—H)

9.4. Cleavage of Protective Groups 1.10 mmol of the product that is produced and purified according to 9.3 is dissolved in 30 ml of methanol and mixed with 10 ml of an 8% aqueous oxalic acid solution. While being stirred, the batch is then heated for 3.5 hours at 60–70° C. in a water bath (reflux condenser). After the mixture is cooled, 40 ml of saturated NaHCO$_3$ solution is added, and it is stirred vigorously for 10 minutes. For working-up, 50 ml of ethyl acetate is added, the organic phase is separated, and the aqueous phase is extracted twice more with ethyl acetate. The combined organic phases are washed with water and semi-concentrated NaCl solution, dried on MgSO$_4$ and liberated of solvent in a vacuum.

Example 24

5-Hydroxy-2-(4-hydroxyphenyl)-3-methyl-1-[10-(pentylsulfinyl)-decyl]-indole (2)

Purification by chromatography on silica gel 60 with ethyl acetate/methanol (30:1) as a mobile solvent.

Greenish solid resin; Yield: 88%; $C_{30}H_{43}NO_3S$ (497.7).

$^1$H-NMR (CDCl$_3$): δ (ppm)=0.63–2.24 (m; 25H; —(CH$_2$)$_8$—, —(CH$_2$)$_3$CH$_3$), 2.10 (s; 3H; Ar—CH$_3$), 2.52–2.95 (m; 4H; SO(CH$_2$—)$_2$), 3.92 (t; $^3$J=7 Hz; 2H; ArN—CH$_2$—), 5.95 (s, br; 1H; —OH), 6.64–7.30 (m; 7H; Ar—H), 8.47 (s, br; 1H; —OH)

5-Hydroxy-2-(4-hydroxyphenyl)-3-methyl-1-[12-(propylsulfinyl)-dodecyl]-indole

Purification by chromatography on silica gel 60 with ethyl acetate/methanol (30:1) as a mobile solvent.

Brownish resin; Yield: 83%; $C_{30}H_{43}NO_3S$ (497.7).

$^1$H-NMR (CDCl$_3$): δ (ppm)=0.80–2.26 (m; 25H; —(CH$_2$)$_{10}$—, —CH$_2$CH$_3$), 2.12 (s; 3H; Ar—CH$_3$), 2.52–2.96 (m; 4H; SO(CH$_2$—)$_2$), 3.95 (t; $^3$J=7 Hz; 2H; ArN—CH$_2$—), 6.67–7.35 (m; 7H; Ar—H)

Example 25

5-Hydroxy-2-(4-hydroxyphenyl)-3-methyl-1-[9-(4,4,5,5,5-pentafluoropentylsulfinyl)-nonyl]-indole (9)

Purification by chromatography on silica gel 60 with ethyl acetate/methanol (30:1) as a mobile solvent.

Greenish solid resin; Yield: 84%; $C_{29}H_{36}F_5NO_3S$ (573.7).

$^1$H-NMR (CDCl$_3$): δ (ppm)=0.84–3.05 (m; 18H; —(CH$_2$)$_7$—, —(CH$_2$)$_2$C$_2$F$_5$), 2.12 (s; 3H; Ar—CH$_3$), 2.55–2.97 (m; 4H; SO(CH$_2$—)$_2$), 3.95 (t; $^3$J=7 Hz; 2H; ArN—CH$_2$—), 6.64–7.36 (m; 7H; Ar—H)

Synthesis of the Benzo[a]carbazole Derivatives
Preparation of the 6,11-dihydro-3,8-dimethoxy-5H-benzo[a]carbazole Parent Substance 10.0 g (57 mmol) of 6-methoxy-1-tetralone in 125 ml of ethanol is added in drops within 35 minutes to a boiling solution of 10.0 g (57 mmol) of p-methoxyphenylhydrazine-hydrochloride and 5.0 ml of concentrated hydrochloric acid in 180 ml of ethanol. Then, it is refluxed for 5 hours. After 370 ml of hot water is added, it is allowed to cool. The almost colorless reaction product is suctioned off and recrystallized from ethanol. Yield 74%, melting point 189–191° C.

Introduction of the Side Chains

The side chains are introduced analogously to the instructions for 2-phenylindole derivatives.

Sodium hydride (0.265 g) is suspended under nitrogen and while being cooled with ice in 75 ml of absolute dimethylformamide (DMF). After about 15 minutes, 1.4 g of benzocarbazole is added in drops to 30 ml of DMF while being cooled with ice. The mixture is stirred until no more gas generation can be detected. Then, the equimolar amount of substituted bromoalkane is added in drops to 25 ml of DMF while being stirred and cooled. After two hours of stirring at room temperature, excess NaH is destroyed by the addition of water. 40 ml of ethyl acetate and 100 ml of water are added, the organic phase is separated and the aqueous phase is shaken out three times with ethyl acetate. The combined organic phases are washed with water, dried on MgSO$_4$ and liberated of solvent in a vacuum. The crude product is purified by column chromatography on silica gel.

Example 26

6,11-Dihydro-3,8-dimethoxy-5H-1-[10-(pentylthio)-decyl]benzo[a]carbazole

Yield: 87%, yellow oil.

$^1$H-NMR (CDCl$_3$): δ (ppm)=0.6–2.15 (m; 25H; alkyl-H), 2.24–2.64 (m; 4H, —CH$_2$SCH$_2$—), 2.78 (m; 4H, —CH$_2$CH$_2$—), 3.70 (s; 3H, OCH$_3$), 3.72 (s; 3H, OCH$_3$), 4.21 (t, J=7 Hz; 2H, NCH$_2$—), 6.52–7.55 (m; 6H, ArH)

Example 27

6,11-Dihydro-3,8-dimethoxy-5H-1-[10-(pentylsulfonyl]-decyl]benzo[a]carbazole

Yield: 34%; amorphous solid.

$^1$H-NMR (CDCl$_3$): δ (ppm)=0.65–2.39 (m; 24H, alkyl-H), 2.55–3.16 (m; 8H, —CH$_2$CH$_2$—, —CH$_2$SO$_2$CH$_2$—), 3.80 (s; 3H, OCH$_3$), 3.86 (s; 3H, OCH$_3$), 4.15–4.51 (m; 2H, NCH$_2$), 6.57–7.60 (m; 6H, ArH)

Ether Cleavage

The ether cleavage is performed according to instructions for 2-phenylindole derivatives. The purification is carried out by column chromatography on silica gel with methylene chloride/ethyl acetate mixtures.

Example 28

6,11-Dihydro-3,8-dihydroxy-5H-1-[10-(pentylthio)-decyl]benzo[a]carbazole (12)

Yield 66%; yellow powder, melting point 116–117° C.
$^1$H-NMR (CDCl$_3$): δ (ppm)=0.65–2.24 (m; 25H, alkyl-H), 2.29–3.05 (m; 8H, —CH$_2$CH$_2$—, —CH$_2$SCH$_2$—), 4.09–4.47 (t, J=7 Hz; 2H, NCH$_2$), 6.3–7.72 (m; 6H, ArH).

Example 29

6,11-Dihydro-3,8-dimethoxy-5H-1-[10 (pentylsulfonyl)-decyl]benzo[a]carbazole (13)

Yield: 83%; yellowish solid, melting point 130–131° C.
$^1$H-NMR (d$_6$-DMSO) δ (ppm)=0.63–2.18 (m; 25H, alkyl-H); 2.60–2.80 (m; 4H,—CH$_2$CH$_2$—), 281–3.20 (m; 4H, —CH$_2$SO$_2$CH$_2$—), 4.05–4.51 (m; 2H, NCH$_2$—), 6.41–7.61 (m; 6H, ArH), 8.59 (s; 1H, —OH), 9.40 (s; 1H, —OH)

What is claimed is:

1. A 2-Phenylindole of formula I

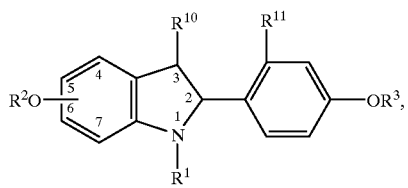

(I)

n which
R$^1$ is —(CH$_2$)$_n$—S(O)$_m$—R$^4$, —(CH$_2$)$_n$—NR$^6$—SO$_2$—R$^4$, or

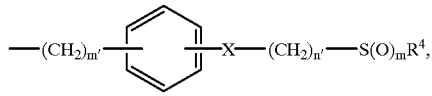

wherein n and n' are integers from 4 to 12 and m and m' are 0, 1 or 2, and X stands for a methylene group, an imino group =NR$^6$, or an oxygen or sulfur atom, R$^2$ and R$^3$, independently of one another, mean a hydrogen atom, a C$_1$ to C$_{10}$ alkyl group, a benzyl, alkanoyl or alkanoyloxy or carbarnoyl radical of formula —C(O)R$^5$ or —C(O)NR$^6$R$^7$ or a tetrahydropyranyl group, R$^4$ means a hydrogen atom, a C$_1$ to C$_{10}$ alkyl group, a completely or partially fluorinated alkyl group —(CH$_2$)$_o$—(CF$_2$)$_p$CF$_3$, whereby o and p, independently of one another, are in each case an integer from 0 to 6, an (alkyl)amino or (alkyl)carbamoyl group of formula —(CH$_2$)$_q$—Y—NR$^8$R$^9$, whereby q is an integer from 0 to 6 and Y stands for a direct bond, a methylene or carbonyl group, or phenyl, naphthyl, benzyl, phenylethyl, naphthylmethyl, pyridinyl, imidazolyl optionally substituted by C1–4-alkyl, pyrazinyl, pyrimidinyl, or thienyl, but if Y means a carbonyl group and m is 2, q cannot be 0, R$^5$ means a C$_1$ to C$_{10}$ alkyl or C$_1$ to C$_{10}$ alkyloxy group, or a phenyl or benzyl radical, R$^6$, R$^7$, R$^8$ and R$^9$, independently of one another, mean a hydrogen atom, or a C$_1$ to C$_{10}$ alkyl or benzyl group, and R$^{10}$ and R$^{11}$ together mean a di-, tri- or tetramethylene bridge, which also can have a C—C double bond anywhere in the bridge.

2. A 2-Phenylindole according to claim 1, wherein R$^1$ is —(CH$_2$)$_n$—S(O)$_m$—R$^4$ or —(CH$_2$)$_n$—NR$^6$—SO$_2$—R$^4$.

3. A 2-Phenylindole according to claim 2, wherein n is an integer from 4 to 12.

4. A 2-Phenylindole according to claim 1, wherein R$^2$ and R$^3$ each are a methyl group.

5. A 2-Phenylindole according to claim 1, wherein R$^2$ and R$^3$ each are a hydrogen atom.

6. A 2-Phenylindole according to claim 1, wherein R$^{10}$ and R$^{11}$ together form an ethano or etheno bridge.

7. A 2-Phenylindole according to claim 2, wherein R$^4$ is a C$_3$ to C$_5$ alkyl group.

8. A 2-Phenylindole according to claim 2, wherein R$^4$ is a completely or partially fluorinated alkyl group —(CH$_2$)$_o$(CF$_2$)$_p$CF$_3$ with o=0, 1, 2, 3 or 4 and p=0, 1, 2, or 3.

9. A 2-Phenylindole according to claim 2, wherein R$^4$ is a phenyl or benzyl radical.

10. A 2-Phenylindole according to claim 2, wherein R$^4$ is a 2-pyridinyl radical.

11. A 2-Phenylindole according to claim 2, wherein m=0 and R$^4$ is a hydrogen atom.

12. A 2-Phenylindole according to claim 2, wherein q=0 and Y is a direct bond.

13. A 2-Phenylindole according to claim 2, wherein q=2, 3, 4 or 5 and Y is a carbonyl group.

14. A 2-Phenylindole according to claim 12, wherein m=2.

15. A 2-Phenylindole according to claim 13, wherein m=0.

16. A 2-Phenylindole according to one of claims 12 to 15 above, wherein R$^8$ is a methyl group and R$^9$ is an n-butyl group.

17. A 2-Phenylindole according to claim 2, wherein R$^1$ is
—(CH$_2$)$_{10}$—S—(CH$_2$)$_4$CH$_3$
—(CH$_2$)$_{10}$—SO—(CH$_2$)$_4$CH$_3$
—(CH$_2$)$_{10}$—SO$_2$—(CH$_2$)$_4$CH$_3$
—(CH$_2$)$_{12}$—SO$_2$—(CH$_2$)$_2$CH$_3$
—(CH$_2$)$_{12}$—SO$_2$—(CH$_2$)$_2$CH$_3$
—(CH$_2$)$_8$—S—(2-pyridinyl)
—(CH$_2$)$_{10}$—S—[2-(N-methyl)imidazolyl
—(CH$_2$)$_{11}$—N(—CH$_3$)—SO$_2$—(CH$_2$)$_2$CH$_3$
—(CH$_2$)$_{11}$—N(—CH$_3$)—SO$_2$—CH$_2$-phenyl
—(CH$_2$)$_{10}$—SO$_2$—N(—CH$_3$)—(CH$_2$)$_3$CH$_3$
—(CH$_2$)$_9$—SO—(CH$_2$)$_3$C$_2$F$_5$
—(CH$_2$)$_9$—SO$_2$—(CH$_2$)$_3$C$_2$F$_5$
—(CH$_2$)$_{10}$—S—CH$_2$—CO—N(—CH$_3$)—CH(CH$_3$)$_2$
—CH$_2$-p-C$_6$H$_4$—O—(CH$_2$)$_4$—SO$_2$—C$_5$H$_{11}$ or
—(CH$_2$)$_6$—S—(CH$_2$)$_3$—CON(—CH$_3$)—(CH$_2$)$_3$CH$_3$.

18. A Compound according to claim 1, which is 6,11-dihydro-3,8-dihydroxy-5H-1-[10-(pentylthio)-decyl]benzo[a]carbazole 6,11-dihydro-3,8-dimethoxy-5H-1-[10-(pentylsulfonyl)-decyl]benzo[a]carbazole 6,11-dihydro-3,8-dimethoxy-5H-1-[10-(pentylthio)-decyl]benzo[a]carbazole 6,11-dihydro-3,8-dimethoxy-5H-1-[10-(pentylsulfonyl)-decyl]benzo[a]carbazole 6,11-dihydro-3,8-dihydroxy-5H-1-[10-(pentylsulfinyl)-decyl]benzo[a]carbazole 6,11-dihydro-3,8-dihydroxy-5H-1-[9-(4,4,5,5,5-pentafluoropentylsulfinyl)-nonyl]benzo[a]carbazole 6,11-dihydro-3,8-dihydroxy-5H-1-[9-(4,4,5,5,5-pentafluoropentylsulfonyl)-nonyl]benzo[a]carbazole 6,11-dihydro-3,8-dihydroxy-5H-1-[10-(pentylmethylsuilfamoyl)-decyl]benzo[a]carbazole 6,11-dihydro-3,8-dihydroxy-5H-1-[10-[2-(N-methylimidazolyl)thio]-decyl]benzo[a]carbazole.

19. A pharmaceutical composition comprising a therapeutic effective amount of a compound of claim 1 and an inert carrier.

20. A process for the production of pharmaceutical agents, comprising bringing a compound of formula I according to claim 1 into administrable form by combining with a pharmaceutically acceptable carrier.

21. A method of treating an estrogen-dependent disease in a patient wherein the disease is prostatic hyperplasia, breast cancer, endometrial carcinoma or melanoma comprising administering to said patient an estrogen antagonistic effective amount of a compound of claim 1.

22. A method of treating an estrogen-dependent disease in a patient wherein the disease is anovulatory infertility or osteoporosis comprising administering to said patient an estrogen agonistic effective amount of a compound of claim 1.

* * * * *

UNITED STATES PATENT AND TRADEMARK OFFICE
CERTIFICATE OF CORRECTION

PATENT NO.   : 6,147,105
DATED        : November 14, 2000
INVENTOR(S)  : Erwin Von Angerer et al.

It is certified that error appears in the above-identified patent and that said Letters Patent is hereby corrected as shown below:

Column 23,
Line 38, delete "n which" and replace with -- in which --;
Line 65, delete "substituted by C1-4-alkyl," and insert -- substituted by $C_{1-4}$-alkyl; --;

Column 24,
Line 46, delete "-$(CH_2)_{12}$-$SO_2$-$(CH_2)_2CH_3$" and insert -- $(CH_2)_{12}$-$SO_2(CH_2(CH_2)_2CH_3$ --;

Column 25,
Line 11, delete "(pentylmethylsuilfamoyl)" and insert -- (pentylmethylsulfamoyl) --.

Signed and Sealed this

Eighteenth Day of December, 2001

Attest:

*Attesting Officer*

JAMES E. ROGAN
*Director of the United States Patent and Trademark Office*